United States Patent
Kwong et al.

(10) Patent No.: US 9,647,221 B2
(45) Date of Patent: May 9, 2017

(54) ORGANIC LIGHT-EMITTING DEVICES

(71) Applicant: Universal Display Corporation, Ewing, NJ (US)

(72) Inventors: Raymond Kwong, Plainsboro, NJ (US); Chuanjun Xia, Lawrenceville, NJ (US); Siddharth Harikrishna Mohan, Plainsboro, NJ (US); Kwang-Ohk Cheon, Holland, PA (US); Jason Brooks, Philadelphia, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

(21) Appl. No.: 14/695,833

(22) Filed: Apr. 24, 2015

(65) Prior Publication Data
US 2015/0255738 A1   Sep. 10, 2015

Related U.S. Application Data

(62) Division of application No. 13/182,855, filed on Jul. 14, 2011, now Pat. No. 9,023,420.

(51) Int. Cl.
*H01L 51/00* (2006.01)
*C07F 7/02* (2006.01)
(Continued)

(52) U.S. Cl.
CPC .......... *H01L 51/0094* (2013.01); *C07F 7/025* (2013.01); *C07F 7/28* (2013.01); *C07F 9/005* (2013.01); *C07F 11/005* (2013.01); *H01L 51/006* (2013.01); *H01L 51/0032* (2013.01); *H01L 51/0051* (2013.01);
(Continued)

(58) Field of Classification Search
None
See application file for complete search history.

(56) References Cited

U.S. PATENT DOCUMENTS

| 4,769,292 A | 9/1988 | Tang et al. |
| 5,061,569 A | 10/1991 | VanSlyke et al. |

(Continued)

FOREIGN PATENT DOCUMENTS

| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Robert Vetere
(74) *Attorney, Agent, or Firm* — Duane Morris LLP

(57) ABSTRACT

Organic electronic devices comprising a covalently bonded organic/inorganic composite layer. The composite layer may be formed by the reaction of a metal alkoxide with a charge transport compound having one or more hydroxyl groups. Examples of metal alkoxides that can be used include vanadium alkoxides, molybdenum alkoxides, titanium alkoxides, or silicon alkoxides. This composite layer can be used for any of the various charge conducting layers in an organic electronic device, including the hole injection layer.

16 Claims, 12 Drawing Sheets

(51) Int. Cl.
  *C07F 7/28*    (2006.01)
  *C07F 9/00*    (2006.01)
  *C07F 11/00*   (2006.01)
  *H01L 51/50*   (2006.01)
  *H01L 51/56*   (2006.01)

(52) U.S. Cl.
  CPC ...... *H01L 51/0059* (2013.01); *H01L 51/0061* (2013.01); *H01L 51/0084* (2013.01); *H01L 51/5012* (2013.01); *H01L 51/5016* (2013.01); H01L 51/0003 (2013.01); H01L 51/5056 (2013.01); H01L 51/5072 (2013.01); H01L 51/5088 (2013.01); H01L 51/5092 (2013.01); H01L 51/56 (2013.01); H01L 2251/303 (2013.01); H01L 2251/558 (2013.01); Y10T 428/31678 (2015.04)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0012744 A1 | 1/2003 | Pedersen |
| 2003/0138657 A1 | 7/2003 | Li et al. |
| 2003/0151042 A1 | 8/2003 | Hueschen |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2004/0265253 A1* | 12/2004 | Seo ................. C03C 14/008 424/63 |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0072714 A1* | 3/2009 | Suzuki ................ H01L 51/0026 313/504 |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | | |
|---|---|---|---|
| EP | 2034538 | 3/2009 | |
| JP | 9279135 A1 | 10/1997 | |
| JP | 2005011610 | 1/2005 | |
| JP | 2005075948 A | 3/2005 | |
| JP | WO 2006046678 A1 * | 5/2006 | ............. C09K 11/06 |
| JP | 2007123392 | 5/2007 | |
| JP | 2007254297 | 10/2007 | |
| JP | 2008074939 | 4/2008 | |
| WO | 0139234 | 5/2001 | |
| WO | 0202714 | 1/2002 | |
| WO | 0215645 | 2/2002 | |
| WO | 03040257 | 5/2003 | |
| WO | 03060956 | 7/2003 | |
| WO | 2004093207 | 10/2004 | |
| WO | 2004107822 | 12/2004 | |
| WO | 2005014551 | 2/2005 | |
| WO | 2005019373 | 3/2005 | |
| WO | 2005030900 | 4/2005 | |
| WO | 2005089025 | 9/2005 | |
| WO | 2005123873 | 12/2005 | |
| WO | 2006009024 | 1/2006 | |
| WO | 2006/046678 A1 | 5/2006 | |
| WO | 2006056418 | 6/2006 | |
| WO | 2006072002 | 7/2006 | |
| WO | 2006082742 | 8/2006 | |
| WO | 2006098120 | 9/2006 | |
| WO | 2006100298 | 9/2006 | |
| WO | 2006103874 | 10/2006 | |
| WO | 2006114966 | 11/2006 | |
| WO | 2006115232 A1 | 11/2006 | |
| WO | 2006132173 | 12/2006 | |
| WO | 2007002683 | 1/2007 | |
| WO | 2007004380 | 1/2007 | |
| WO | 2007063754 | 6/2007 | |
| WO | 2007063796 | 6/2007 | |
| WO | 2008056746 | 5/2008 | |
| WO | 2008101842 | 8/2008 | |
| WO | 2008132085 | 11/2008 | |
| WO | 2009000673 | 12/2008 | |
| WO | 2009003898 | 1/2009 | |
| WO | 2009008311 | 1/2009 | |
| WO | 2009018009 | 2/2009 | |
| WO | 2009050290 | 4/2009 | |
| WO | 2009021126 | 5/2009 | |
| WO | 2009062578 | 5/2009 | |
| WO | 2009063833 | 5/2009 | |
| WO | 2009066778 | 5/2009 | |
| WO | 2009066779 | 5/2009 | |
| WO | 2009086028 | 7/2009 | |

(56) References Cited

FOREIGN PATENT DOCUMENTS

| WO | 2009100991 | | 8/2009 |
|---|---|---|---|
| WO | 2011052648 | A1 | 5/2011 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylannine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes Of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162(1996).

(56) References Cited

OTHER PUBLICATIONS

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

European Search Report from European Patent Application No. 12 17 2574, mailed on Oct. 8, 2012.

Suzuki et al., "Polymer/Metal-Oxide Composite: A Novel Buffer Layer for Solution-Processible OLEOs", Semiconductor Energy Laboratory Co., Ltd., 398 Hase, Atsugi-shi, Kanagawa, Japan.1840-1843, SID 07 Digest.

Seo et al., "High-Efficient Green OLEO over 150 lm/W with New P-doped Layer Exhibiting No Optical Loss Derived 2 from Charge Transfer Complex", Semiconductor Energy Laboratory Co., Ltd., 398 Hase, Atsugi-shi, Kanagawa, D Japan.1804-1807, SID 10 Digest.

Ikeda et al., "Low-Drive-Voltage OLEOs with a Buffer Layer Having Molybdenum Oxide", Semiconductor Energy Laboratory Co., Ltd., 398 Hase, Atsugi-shi, Kanagawa, Japan.923-926, SID 06 Digest.

Zhou et al., 2010, "Multilayer structured polymer light emitting diodes with cross-linked polymer matrices", Appl. Phys. Lett. 96:013504-1 to 013504-3.

Zhu et al., 2007, "Investigation of Al- and Ag-Based Top-Emitting Organic Light-Emitting Diodes with Metal Oxides as Dole-Injection Layer", The Japan Society of Appl. Physl, 46(3A):1033-1036.

\* cited by examiner where:
R^16 is a highly-fluorinated alkyl or a highly-fluorinated aryl group;
c is independently 0 or an integer from 1 to 3; and
n is at least 4.

ORGANIC LIGHT-EMITTING DEVICES

CROSS-REFERENCE TO RELATED APPLICATIONS

This application is a divisional application of U.S. patent application Ser. No. 13/182,855, now U.S. Pat. No. 9,023,420 filed Jul. 14, 2011 the disclosure of which is expressly incorporated herein by reference in its entirety.

JOINT RESEARCH AGREEMENT

The claimed invention was made by, on behalf of, and/or in connection with one or more of the following parties to a joint university corporation research agreement: Regents of the University of Michigan, Princeton University, University of Southern California, and Universal Display Corporation. The agreement was in effect on and before the date the claimed invention was made, and the claimed invention was made as a result of activities undertaken within the scope of the agreement.

TECHNICAL FIELD

The present invention relates to organic light emitting devices (OLEDs), and more specifically to organic layers used in such devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule. As used herein, "organic" includes metal complexes of hydrocarbyl and heteroatom-substituted hydrocarbyl ligands.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

SUMMARY

The present invention provides a composite organic/inorganic layer for a charge conducting layer of an organic electronic device. In one embodiment, the present invention provides a method of making a composite organic/inorganic layer for an organic electronic device, comprising: (a) having a solution containing a metal alkoxide and a charge transport compound that includes a hydroxyl group; (b) depositing the solution onto a surface to form a composite organic/inorganic layer; and (c) reacting the charge transport compound with the metal alkoxide to form a covalently bonded composite organic/inorganic layer.

In another embodiment, the present invention provides an organic electronic device comprising: (a) a first electrode; (b) a second electrode; and (c) a covalently bonded composite organic/inorganic layer between the first and second electrodes, wherein the covalently bonded organic/inorganic composite layer is made by the reaction of a metal alkoxide with a charge transport compound having a hydroxyl group.

In another embodiment, the present invention provides a covalently bonded composite organic/inorganic layer comprising a metal-organic material formed by the reaction of a metal alkoxide with a charge transport compound having a hydroxyl group.

DETAILED DESCRIPTION

Figure 1:
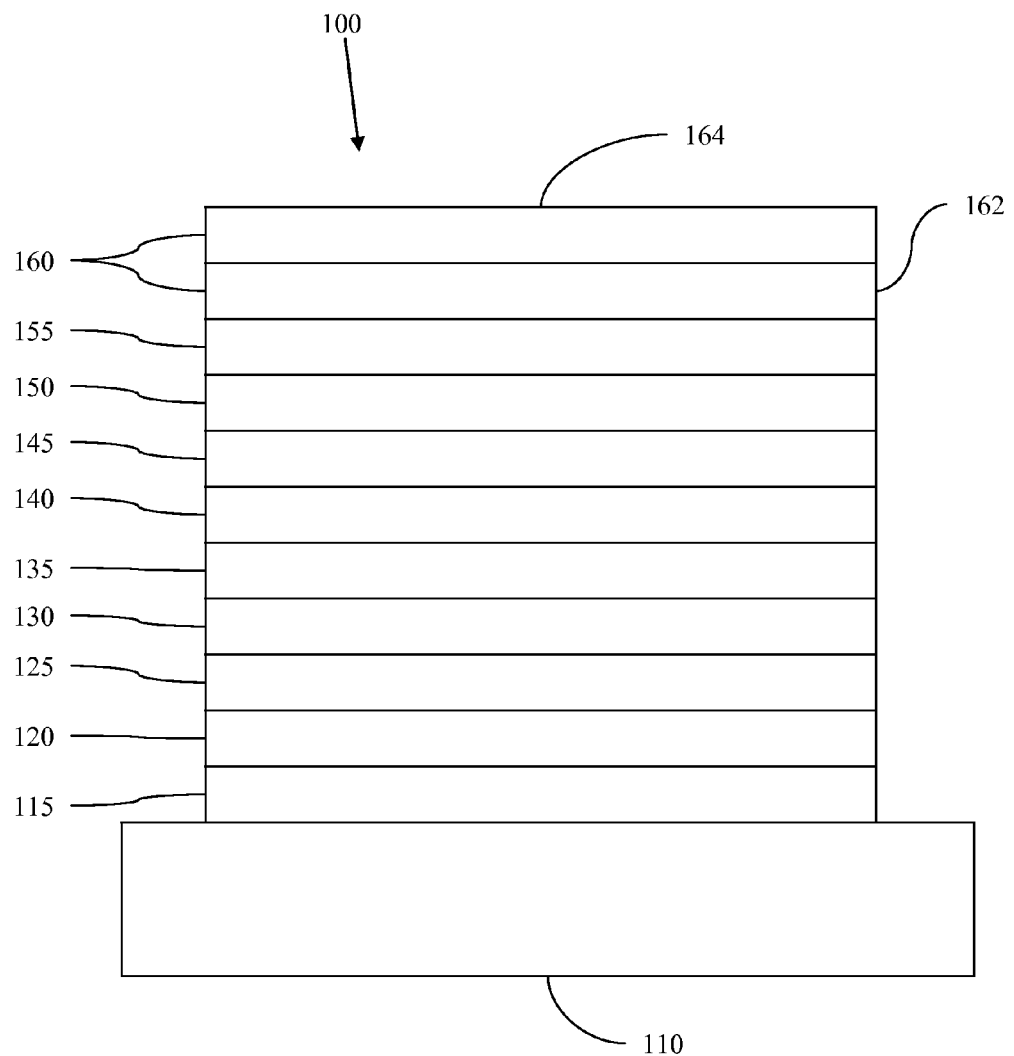
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 1, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organometallic materials such as disclosed in U.S. Pat. Nos. 6,303,238 and 6,310,360; U.S. Patent Application Publication Nos. 2002/0034656; 2002/0182441; 2003/0072964; and PCT publication WO 02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material.

The highest energy feature is not necessarily the peak having the greatest intensity in the phosphorescence spectrum, and could, for example, be a local maximum of a clear shoulder on the high energy side of such a peak.

The term "organometallic" as used herein is as generally understood by one of ordinary skill in the art and as given, for example, in "Inorganic Chemistry" (2nd Edition) by Gary L. Miessler and Donald A. Tan, Prentice Hall (1998). Thus, the term organometallic refers to compounds which have an organic group bonded to a metal through a carbon-metal bond. This class does not include per se coordination compounds, which are substances having only donor bonds from heteroatoms, such as metal complexes of amines, halides, pseudohalides (CN, etc.), and the like. In practice organometallic compounds generally comprise, in addition to one or more carbon-metal bonds to an organic species, one or more donor bonds from a heteroatom. The carbon-metal bond to an organic species refers to a direct bond between a metal and a carbon atom of an organic group, such as phenyl, alkyl, alkenyl, etc., but does not refer to a metal bond to an "inorganic carbon," such as the carbon of CN or CO.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003/0230980 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include Ir(ppy)$_3$. Examples of fluorescent emissive materials include DCM and DMQA. Examples of host materials include Alq$_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the photoactive properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels involved in light emission. A ligand that is photoactive in one molecule may be ancillary in another. These definitions of photoactive and ancillary are intended as non-limiting theories.

Electron transport layer 145 may include a material capable of transporting electrons. Electron transport layer 145 may be intrinsic (undoped), or doped. Doping may be used to enhance conductivity. Alq$_3$ is an example of an intrinsic electron transport layer. An example of an n-doped electron transport layer is Bphen doped with Li at a molar ratio of 1:1, as disclosed in U.S. Patent Application Publication No. 2003/0230980 to Forrest et al., which is incorporated by reference in its entirety. Other electron transport layers may be used.

The charge carrying component of the electron transport layer may be selected such that electrons can be efficiently injected from the cathode into the LUMO (lowest unoccupied molecular orbital) energy level of the electron transport layer. The "charge carrying component" is the material responsible for the LUMO energy level that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436; 5,707,745; 6,548,956; and 6,576,134, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2003/0230980 to Forrest et al., which are incorporated by reference in their entireties.

As used herein, and as would be understood by one skilled in the art, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. Pat. No. 7,071,615 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (highest occupied molecular orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO energy level that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface.

However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. Pat. No. 7,071,615 to Lu et al., which is incorporated by reference in its entirety.

Figure 2:
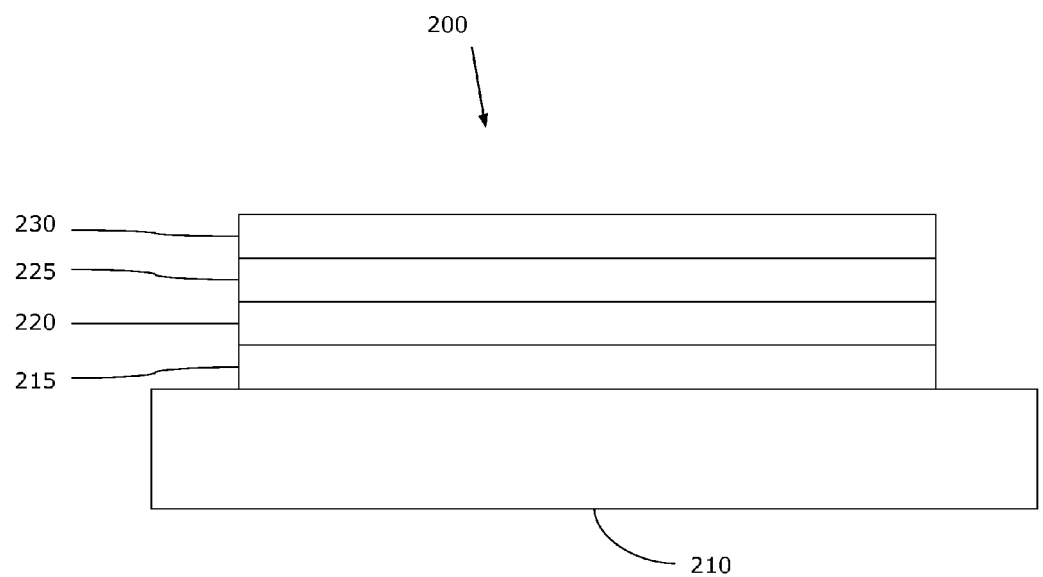
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968 to Shtein et al., which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJP. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention. For example, substituents may be added to a compound having three bidentate ligands, such that after the substituents are added, one or more of the bidentate ligands are linked together to form, for example, a tetradentate or hexadentate ligand. Other such linkages may be formed. It is believed that this type of linking may increase stability relative to a similar compound without linking, due to what is generally understood in the art as a "chelating effect."

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18-30° C., and more preferably at room temperature (20-25° C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In one aspect, the present invention provides an organic electronic device comprising a covalently bonded composite organic/inorganic layer as a charge conducting layer. The composite organic/inorganic layer comprises a metal-organic material with covalent metal-oxygen-carbon bonds (e.g., via cross-linking or polymerization). This is in contrast to pure metal-oxide materials having only metal-oxygen bonds. The composite organic/inorganic layer of the present invention can be made using any suitable method.

Figure 3:
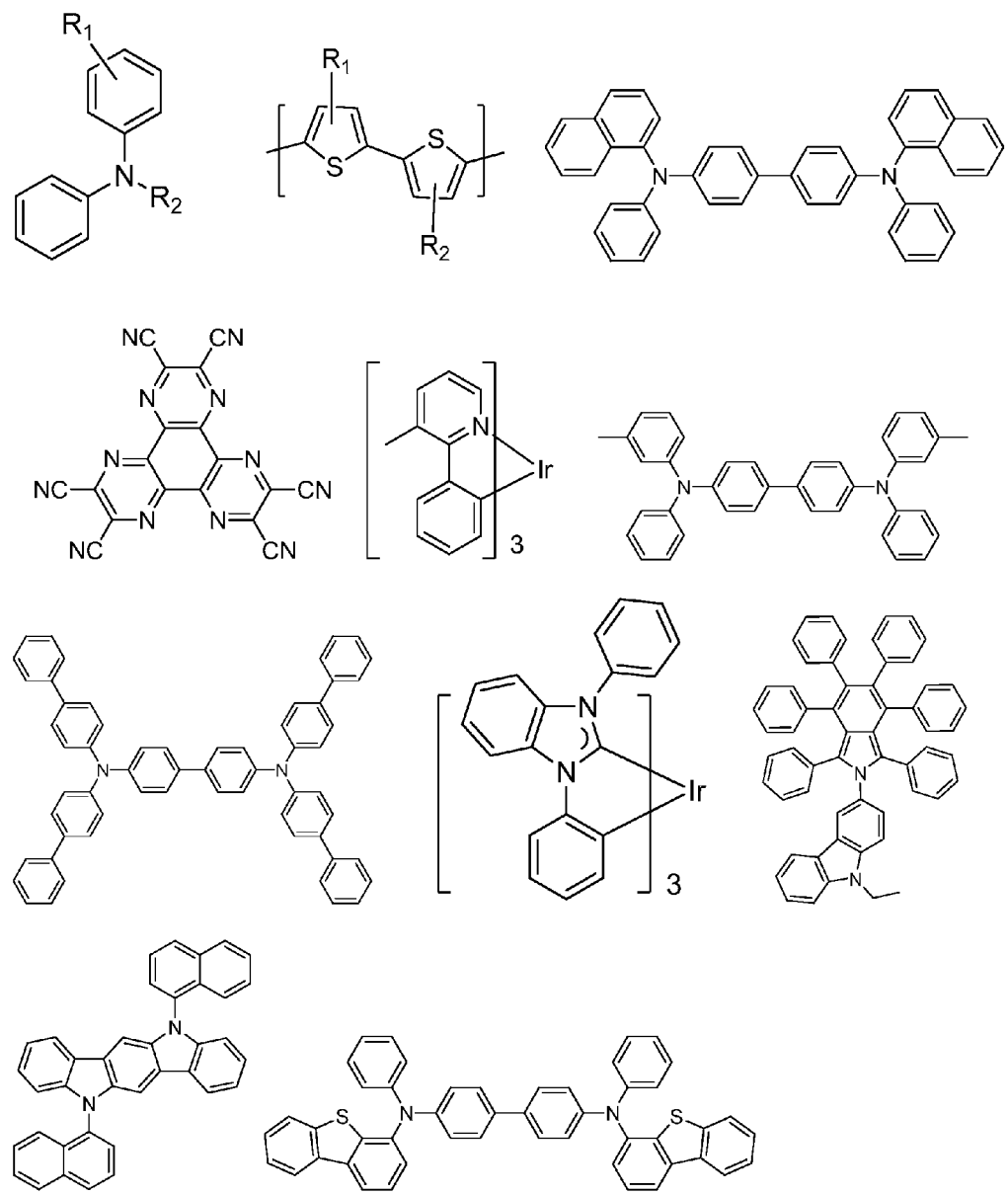
FIG. 3 shows examples of charge transporting compounds to which hydroxyl groups can be added for use in the present invention.
Figure 3:
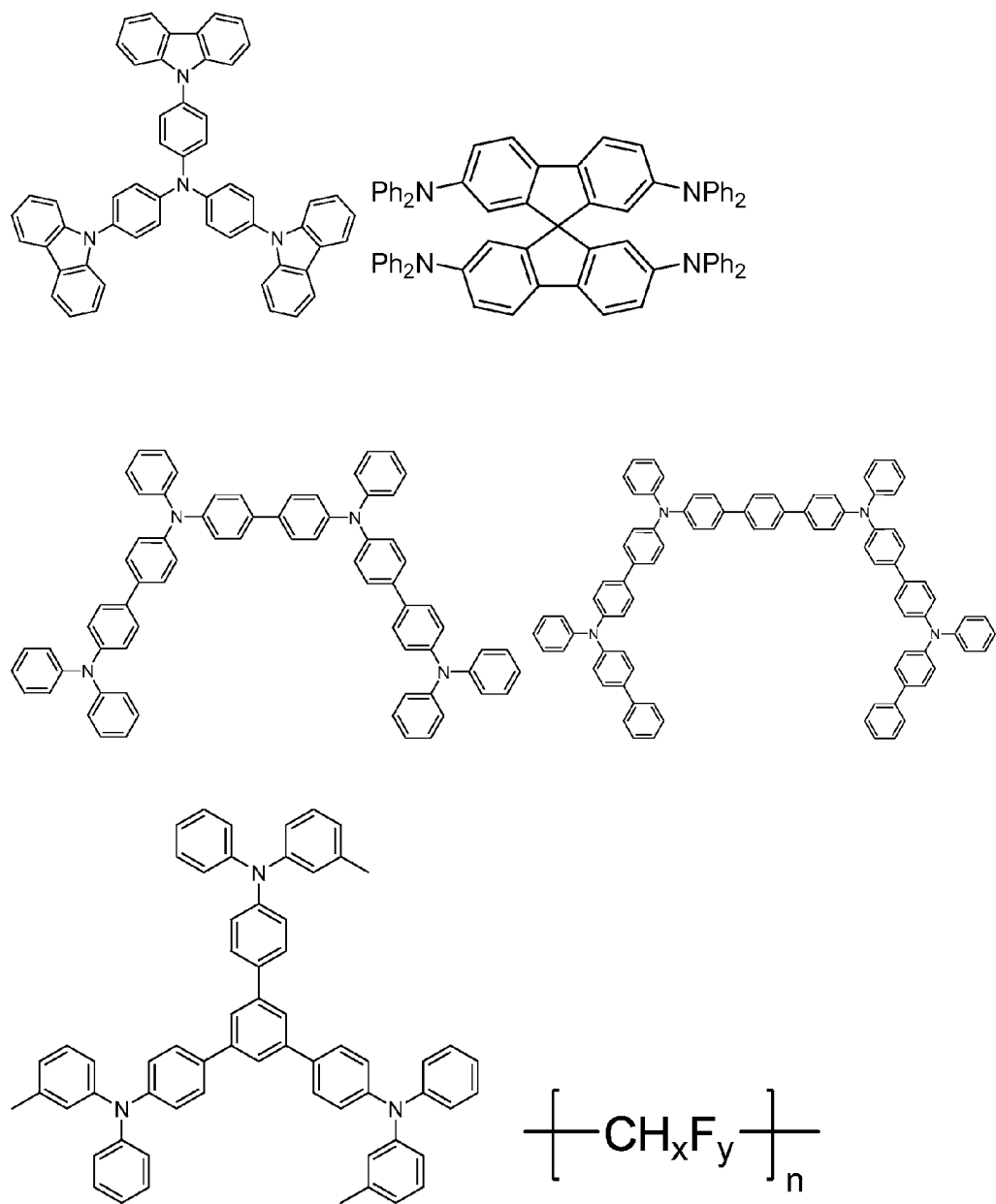
Figure 3:
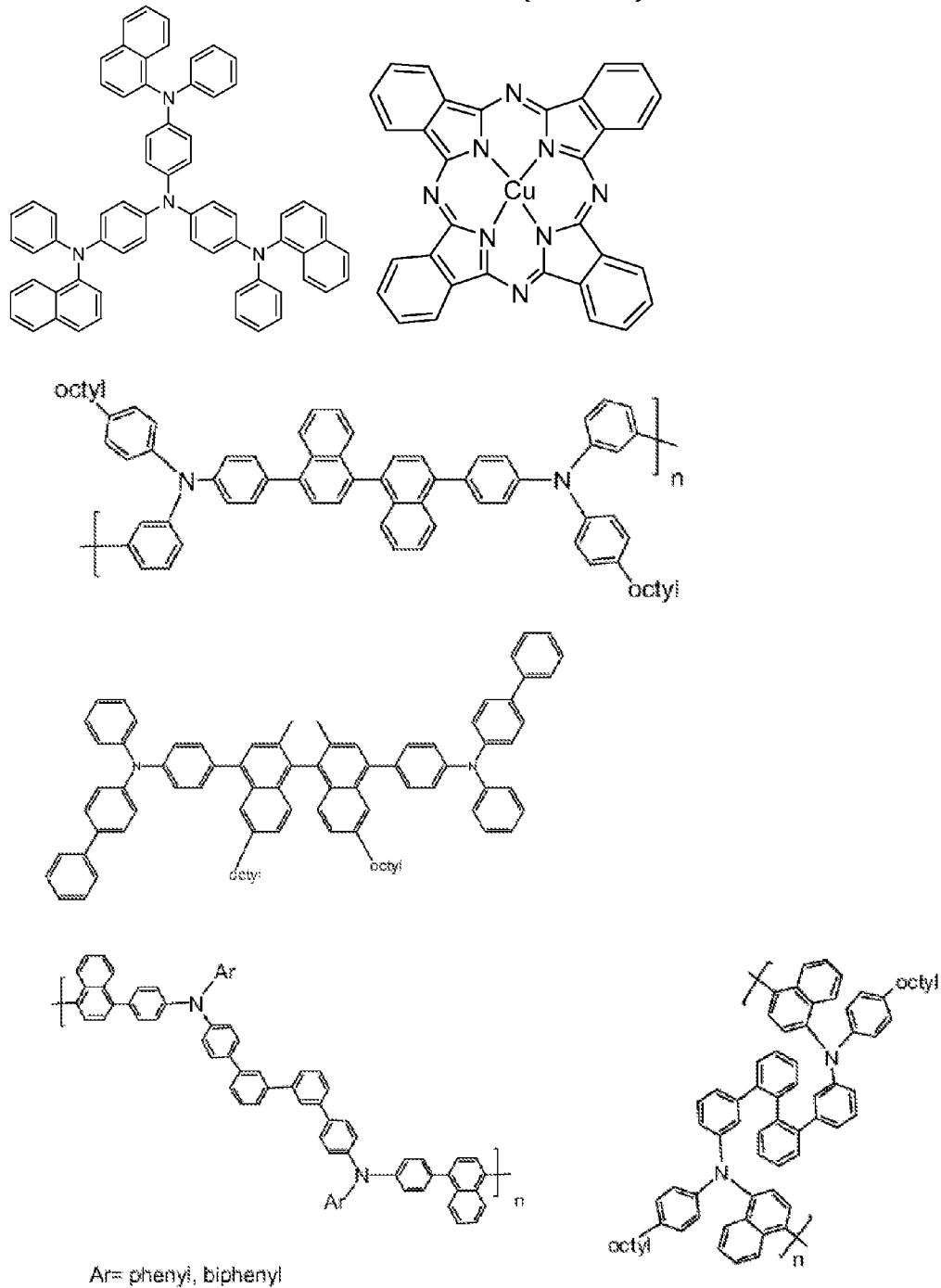
Figure 3:
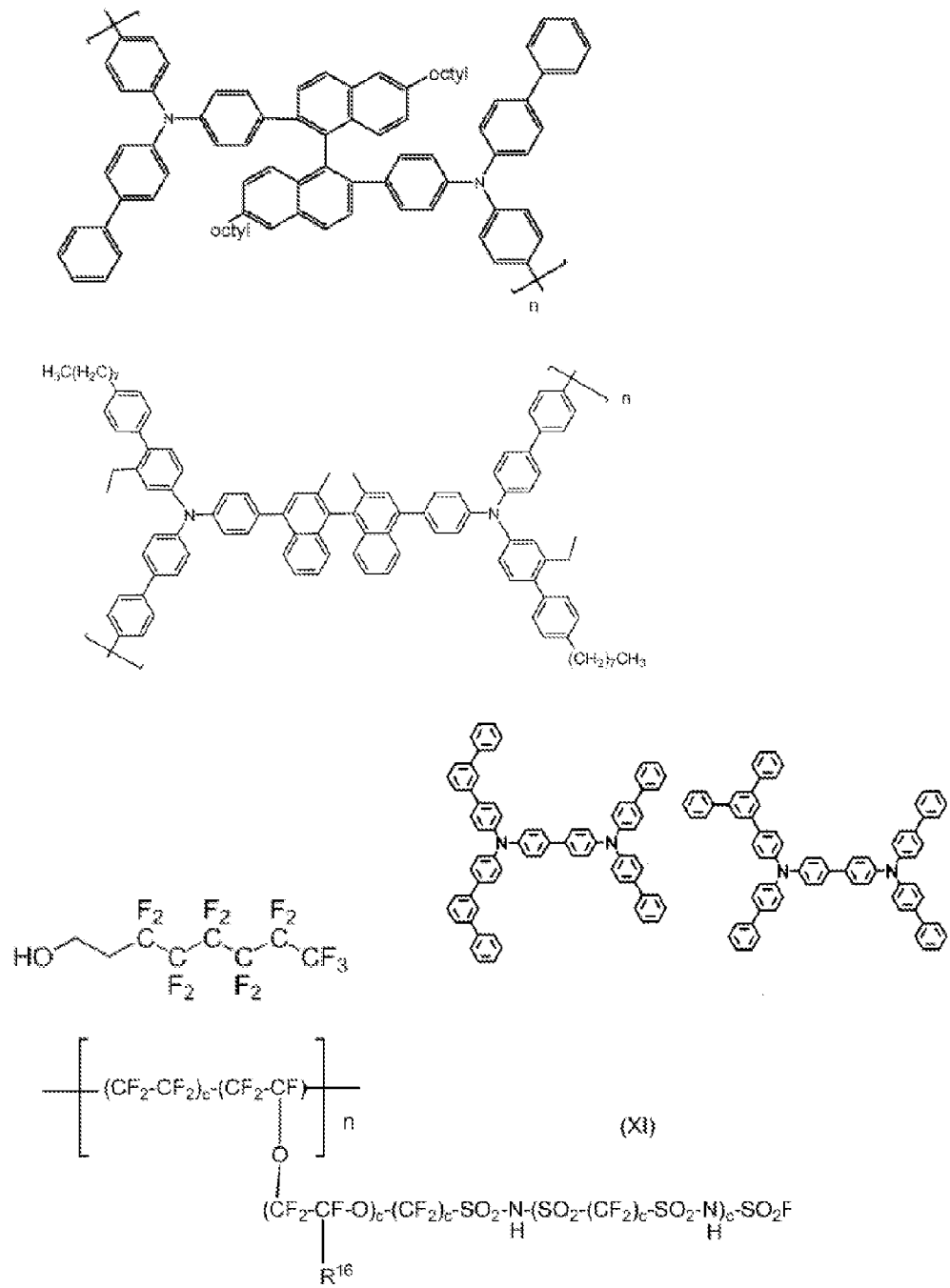
Figure 3:
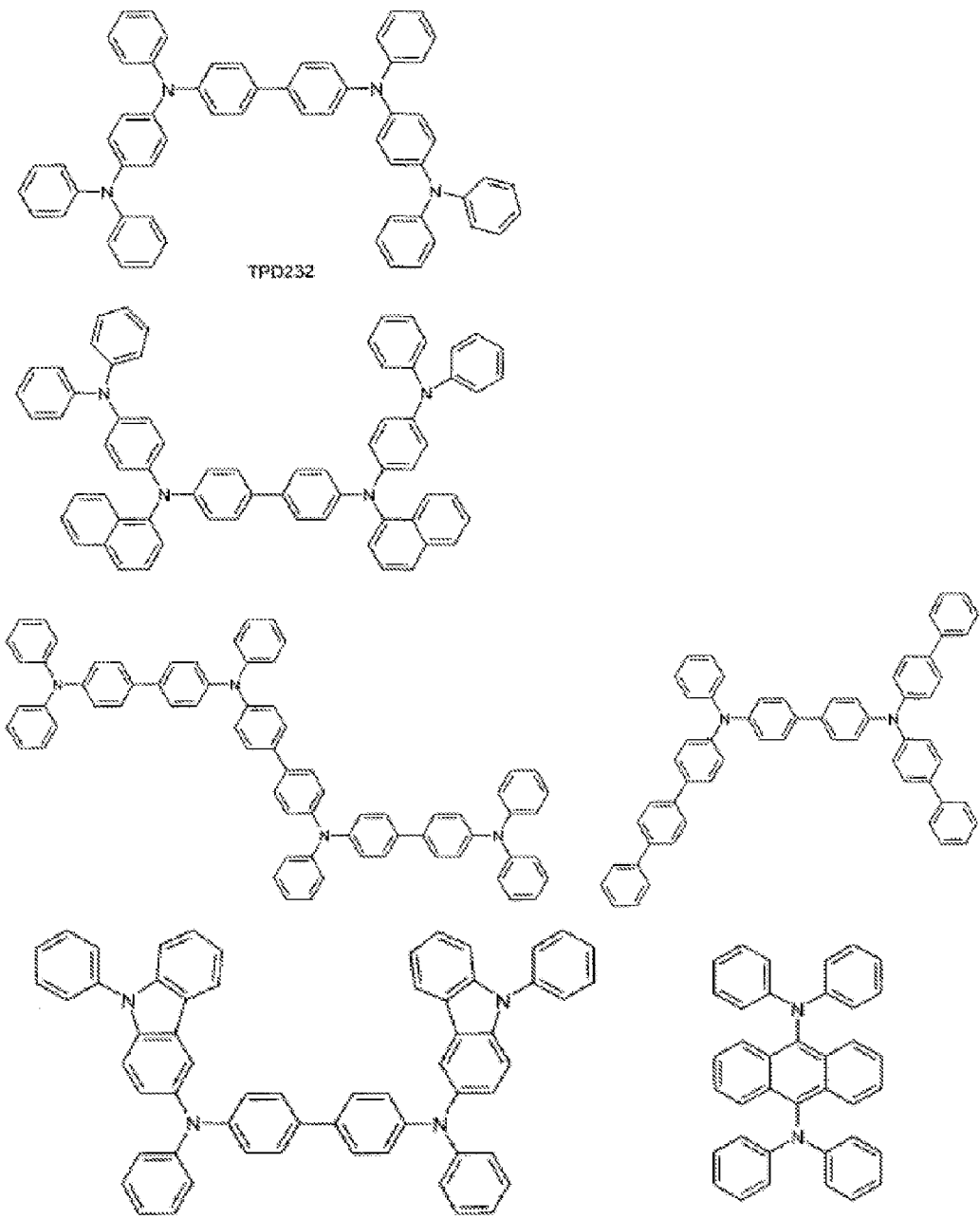
Figure 3:
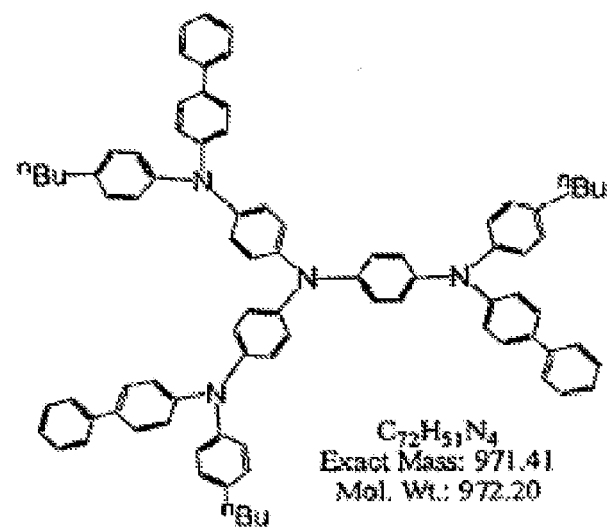
Figure 3:
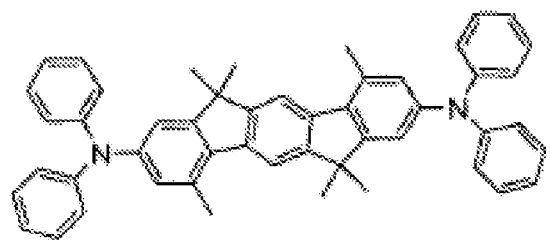
Figure 3:
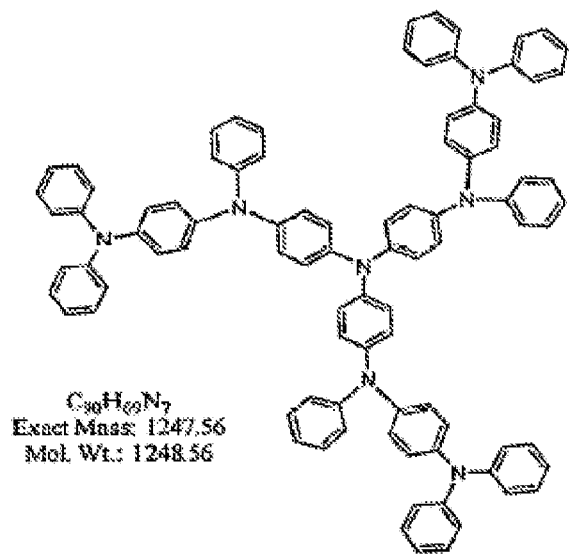
Figure 3:
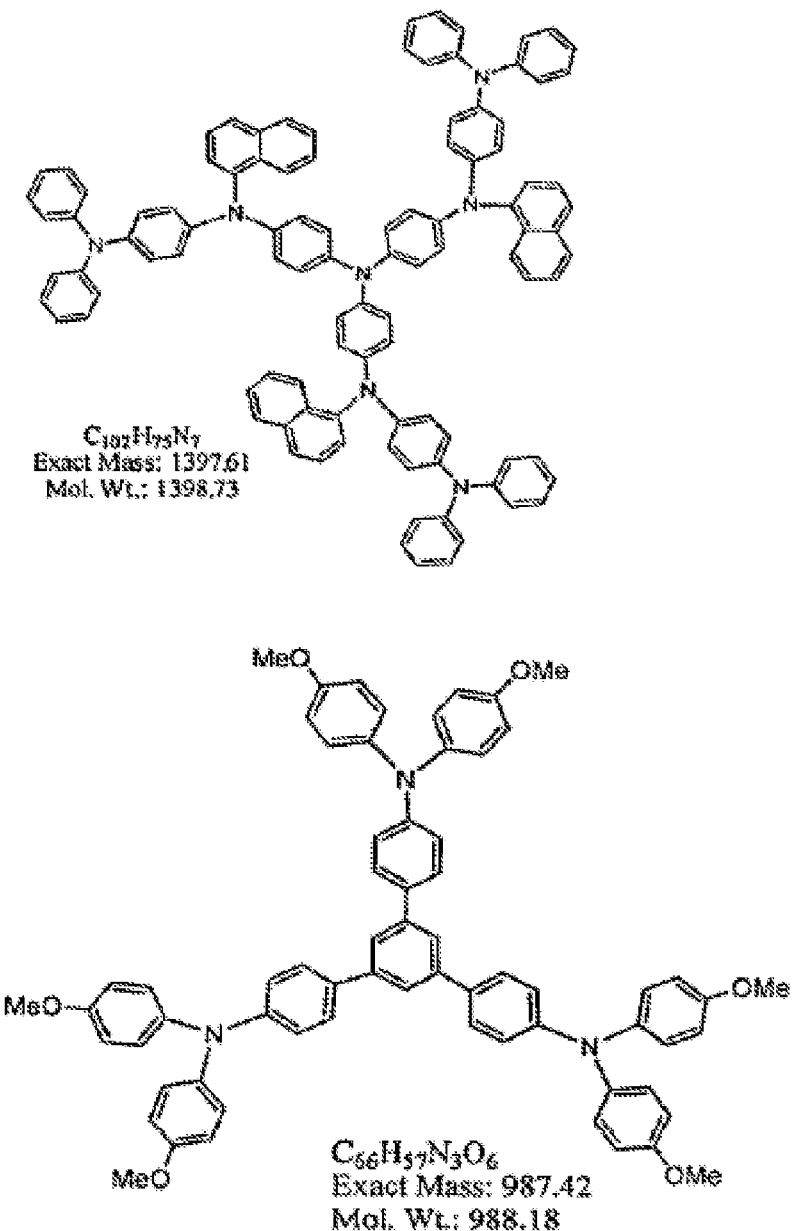
Figure 3:
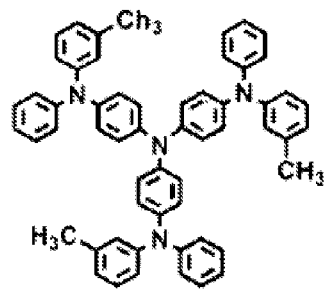
Figure 3:
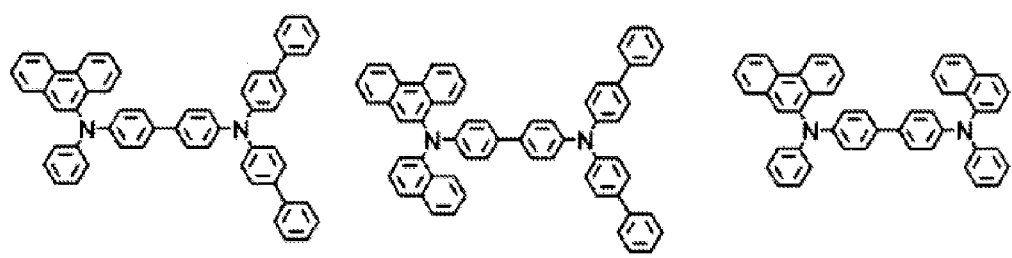
Figure 3:
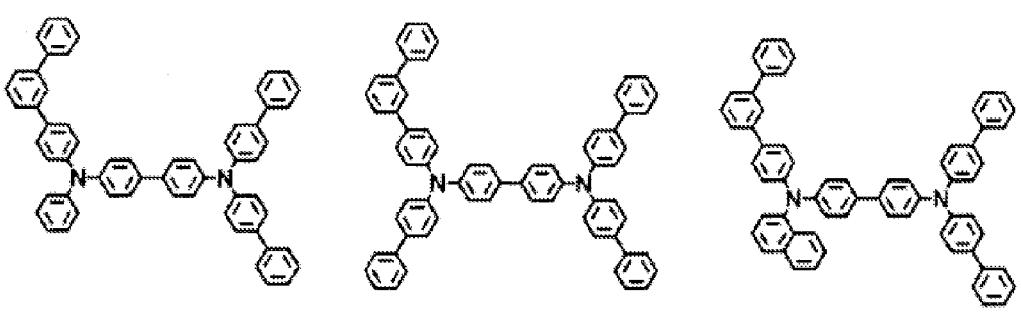
Figure 3:
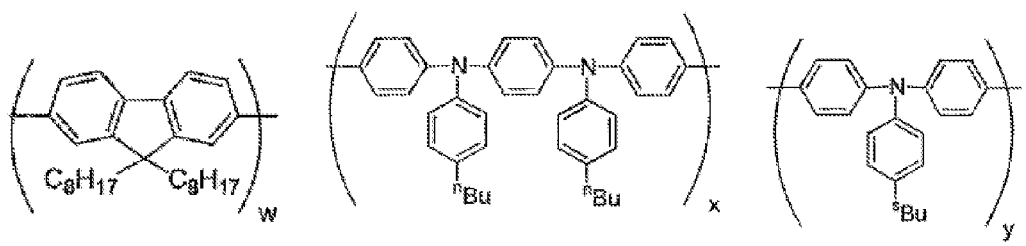
Figure 3:
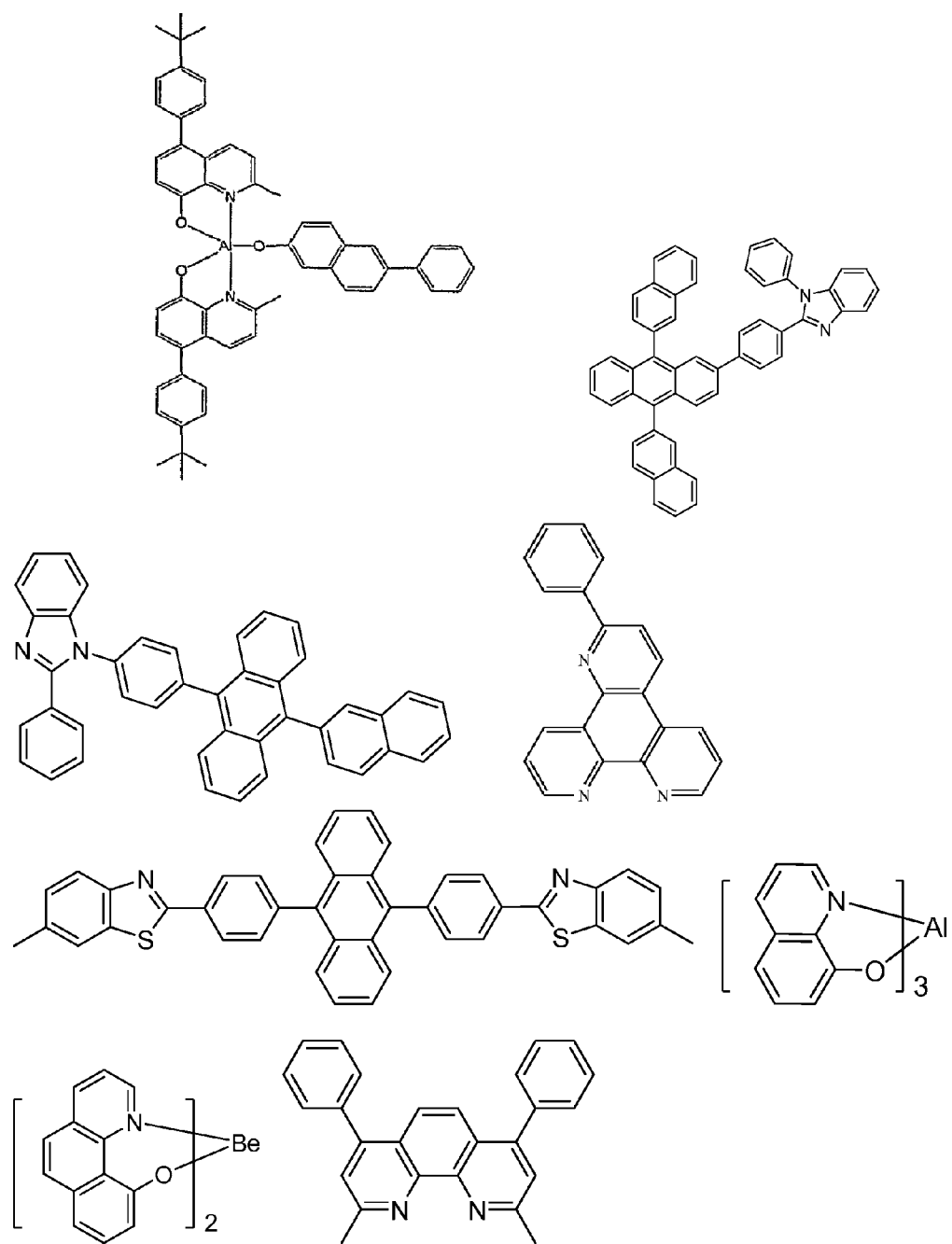
Figure 3:
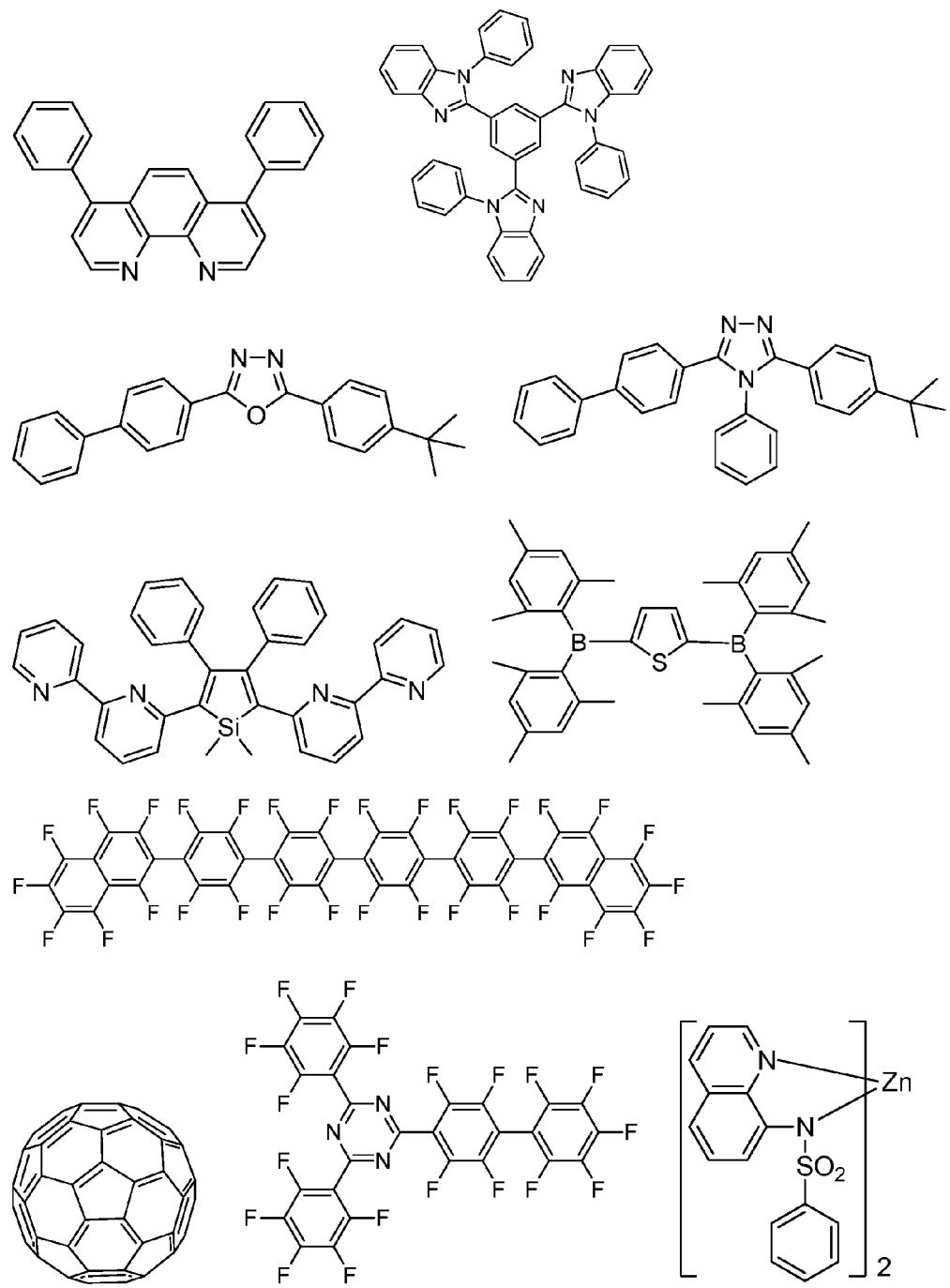

In one embodiment, the composite layer is made by the reaction of a metal alkoxide with a charge transport compound having one or more hydroxyl groups. A variety of different kinds of charge transport compounds (with hydroxyl group(s)) may be suitable for use in the present invention. The charge transport compound may be hole transporting, electron transporting, or both. Examples of charge transporting compounds to which hydroxyl groups can be added for use in the present invention are shown in FIG. 3. In some cases, the charge transporting compound of the present invention is a metal complex. In some cases, the charge transporting compound of the present invention is a hole transporting compound having one or more triarylamine moieties. There may be more than one type of metal alkoxide and/or more than one type of charge transport compound having hydroxyl group(s) involved in making the composite layer.

The hydroxyl group(s) on the charge transport compound promote the reaction with the metal alkoxide to form a covalent bond. The metal in the metal alkoxide may be any of the various metals suitable for use in charge conducting layers of an organic electronic device. Examples of metal elements that can be used include vanadium, molybdenum, titanium, or silicon (although not conventionally referred to as a "metal," for the sake of convenience, the term "metal" is intended to include silicon), i.e., the metal alkoxide can be vanadium alkoxide, molybdenum alkoxide, titanium alkoxide, or silicon alkoxide. The metal atom in the metal alkoxide may have a relatively high valency state, which can be particularly useful for increasing the electron affinity of the metal alkoxide (which may enhance conductivity) and/or increasing the number of cross-linking sites. In some cases, the metal has an oxidation state of at least 2 in the metal alkoxide. In some cases, the metal may be selected from one of the transition metals of groups 3, 4, 5, or 6. In some cases, the alkyl moieties in the alkoxide have 1-15 carbon atoms.

Any of various types of organic solvents, such as cyclohexanone, may be suitable for making the composite layer of the present invention. The amount of metal alkoxide material relative to the hydroxylated-charge transport compound material in the solution will vary depending upon the particular application. In some cases, the molar ratio of the metal alkoxide material to the hydroxylated-charge transport compound material is 1:1 to 1:3.

The color of the solution may change when the metal alkoxide and the charge transport compound are combined. This color change may be the result of light absorption when the metal alkoxide and the charge transport compound combine to form a donor-acceptor charge transfer complex (with the charge transport compound acting as an electron donor, and the metal alkoxide acting as the electron acceptor). This may result in the absorption spectrum of the solution being shifted towards longer wavelengths (lower energy). In some cases, the absorption spectrum of the color-changed solution has an absorption band that includes wavelengths greater than 700 nm.

The solution is deposited onto a surface to form a composite organic/inorganic layer. Deposition of the solution may be performed by any suitable solution deposition technique, including spin coating, spray coating, dip coating, slot coating, nozzle printing, or inkjet printing. The covalently bonded composite organic/inorganic layer is formed when the metal alkoxide material reacts with the charge transport compound material via its hydroxyl group(s) to form covalent bonds. The resulting composite organic/inorganic layer is made of a metal-organic material with covalent metal-oxygen-carbon bonds (e.g., via cross-linking or polymerization). This reaction may be accelerated by various means, including heating of the deposited solution.

In some cases, the drying and/or heating of the deposited film may be performed in an atmosphere containing amounts of oxygen and/or moisture that would have damaging effects on materials that are conventionally used to make organic layers or interfere with good film formation. In conventional methods, the layer deposition process may require an inert atmosphere (e.g., inside a glove box) to minimize the adverse effects of oxygen and/or moisture. However, in the present invention, since the metal alkoxide is already in oxidized form, proper reaction or formation of the composite layer is less sensitive to the presence of oxygen. Also, the presence of moisture can promote the hydrolysis of the metal alkoxides. As such, in some cases, the deposition, drying and/or heating the solution may be performed in an atmosphere containing at least 18% oxygen, or at least 5% relative humidity, or both, and still result in good film formation. In some cases, the deposited solution may be dried and/or heated in ambient air. For example, the heating may be performed without requiring an inert atmosphere in a glove box.

The composite layer may be used for any of the various charge conducting layers of an organic electronic device. For example, the composite layer may serve as the hole injection layer, hole transport layer, electron injection layer, or electron transport layer. In some cases, the composite layer of the present invention is a charge injection layer, such as a hole injection layer or electron injection layer. The charge injection layer may be directly adjacent one of the electrodes (e.g., directly adjacent the cathode if electron injecting, or directly adjacent the anode if hole injecting).

In some cases, the composite layer is a hole injection layer and this hole injection layer may have any suitable thickness. The composite layer of the present invention may be sufficiently conductive to allow relatively thicker hole injection layers. In some cases, the hole injection layer has a thickness in the range of 50-750 Å; and in some cases, in the range of 300-750 Å. Relatively thicker hole injection layers have the advantage of allowing better coverage of rough surfaces without short circuit defects. In an organic light-emitting device, having relatively thicker hole injection layers can also be useful for providing microcavity effects that enhance color saturation.

A composite organic/inorganic layer formed of a covalently bonded matrix can be useful in the fabrication of organic electronic devices by solution processing techniques, such as spin coating, spray coating, dip coating, ink jet, and the like. In solution processing, the organic layers are deposited in a solvent. Therefore, in a multi-layered structure, any underlying layer is preferably resistant to the solvent that is being deposited upon it. Thus, in certain embodiments, the covalent bonding of the charge transport compound and the metal alkoxide in the composite layer can render the composite layer resistant to solvents. As such, the composite layer can avoid being dissolved, morphologically influenced, or degraded by a solvent that is deposited over it.

EXPERIMENTAL

Specific representative embodiments of the invention will now be described, including how such embodiments may be made. It is understood that the specific methods, materials, conditions, process parameters, apparatus and the like do not necessarily limit the scope of the invention.

Example organic light-emitting devices were fabricated using the following Compound A as a hydroxylated hole transport compound and the following metal alkoxides to make the hole injection layer:

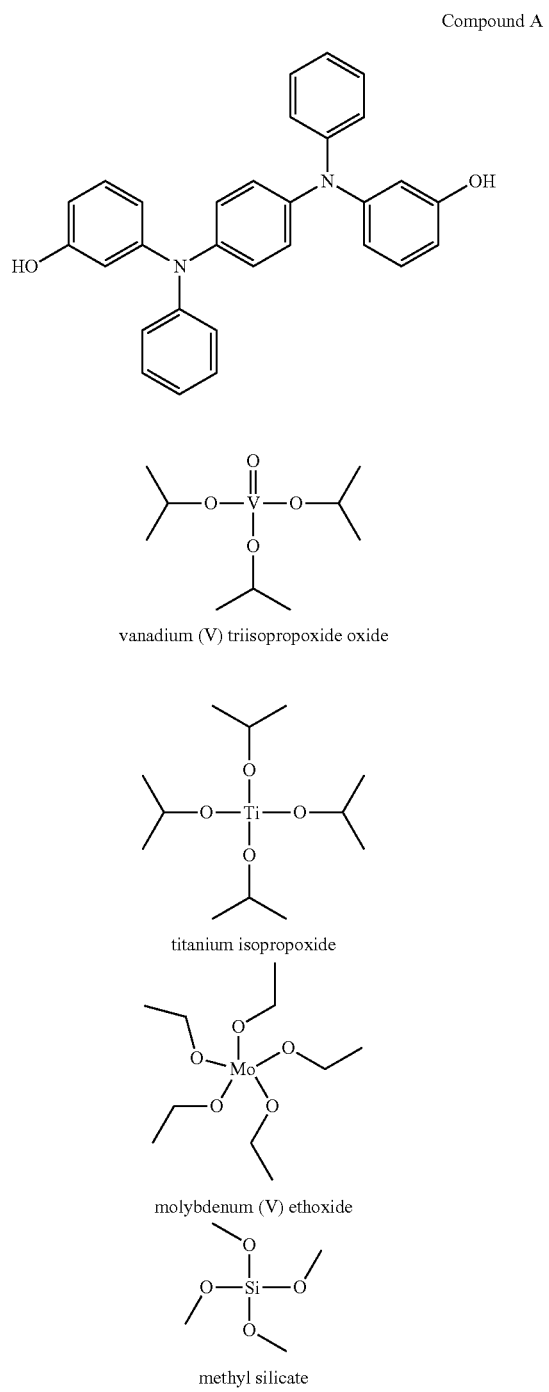

vanadium (V) triisopropoxide oxide titanium isopropoxide molybdenum (V) ethoxide methyl silicate Preparation of Hole Injection Layer HIL1: Isopropoxyvanadium oxide (0.225 mol) was dissolved in 5 mL of cyclohexanone. Compound A (0.45 mol) was dissolved in 5 mL of cyclohexanone and was added to the vanadium solution. The solution (molar ratio 1:2 of isopropoxyvanadium oxide:compound A) turned dark green and was vigorously stirred overnight. The concentration of the resulting solution was adjusted (by diluting with cyclohexanone) to yield a thickness of 150 Å when spin coated at 4000 rpm for 40 seconds. The resulting film was baked in air for 30 minutes at 200° C. After baking, the film became insoluble. This resulting film is labeled HIL1.

Preparation of Hole Injection Layer HIL2: Molybdenum (V) ethoxide (0.225 mol) was dissolved in 5 mL of cyclohexanone. Compound A (0.45 mol) was dissolved in 5 mL of cyclohexanone and was added to the vanadium solution. The solution (molar ratio 1:2 of molybdenum ethoxide:compound A) turned brown and was vigorously stirred overnight. The concentration of the resulting solution was adjusted (by diluting with cyclohexanone) to yield a thickness of 115 Å when spin coated at 3000 rpm for 40 seconds. The resulting film was baked in air for 30 minutes at 200° C. After baking, the film became insoluble. This resulting film is labeled HIL2.

Preparation of Hole Injection Layer (Comparative) HIL3: For the comparative devices, hole injecting material Compound B along with Conducting dopant-1 (see below) were dissolved in cyclohexanone solvent. The amount of Conducting dopant-1 in the solution was 10 wt % relative to Compound B. The total concentration of the Compound B and Conducting dopant-1 was 0.5 wt % in cyclohexanone. The solution was spin-coated at 4000 rpm for 60 seconds onto a patterned indium tin oxide (ITO) electrode. The resulting film was baked in a glovebox for 30 minutes at 250° C. The film was insoluble after baking. The resulting film is labeled HIL3.

Preparation of Hole Injection Layer (Comparative) HIL PEDOT: PSS: Low conductivity PEDOT:PSS (purchased from Sigma-Aldrich Corp.) was diluted with deionized water. The solution was spin coated at 4000 rpm and baked in air for 10 minutes at 200° C.

Organic light-emitting devices were made using the hole injection layers described above. The hole injection layers were made on an ITO substrate, and then a hole transporting layer (HTL), and then emissive layer (EML) were formed by spin-coating. Blocking layers and electron transport layers were made by vapor deposition. The HTL was made by spin-coating a 0.5 wt % solution of the hole transporting material HTL1 (see below) in toluene at 4000 rpm for 60 seconds. The HTL film was baked at 200° C. for 30 minutes. After baking, the HTL became an insoluble film.

To form the EML, a toluene solution containing Host-1 and Green Dopant-1 (net concentration of 0.75 wt % in toluene), with Host-1:Green Dopant-1 weight ratio of 88:12, was spin-coated on top of the insoluble HTL at 1000 rpm for 60 seconds, and then baked at 80° C. for 60 minutes to remove solvent residues. To form the blocking layer (BL) and electron transport layer (ETL), a 50 Å hole blocking layer containing compound BL1 or BL2 (see below) is vapor deposited on the EML. Subsequently, a 350 Å electron transport layer containing LG201 (LG Chemical Corp.) is vapor deposited. This is followed by an electron injection layer containing LiF, and an aluminum electrode (cathode) that were sequentially vacuum deposited in a conventional fashion.

The following devices were made according to the above descriptions:
    Device 1: HIL1/HTL1/Host-1:Green Dopant-1(88:12)/ BL1/LG201
    Device 2: HIL2/HTL1/Host-1:Green Dopant-1(88:12)/ BL1/LG201
    Device 3: HIL1/HTL1/Host-1:Green Dopant-1(88:12)/ BL2/LG201

Device 4: HIL2/HTL1/Host-1:Green Dopant-1(88:12)/BL2/LG201
Comparative Device 5: HIL3/HTL1/Host-1:Green Dopant-1(88:12)/BL1/LG201
Comparative Device 6: HIL3/HTL1/Host-1:Green Dopant-1(88:12)/BL2/LG201
Comparative Device 7: PEDOT:PSS/HTL1/Host-1:Green Dopant-1(88:12)/BL2/LG201

The performances of the devices were tested by operation under a constant DC current. Table 1 below summarizes the performance of the devices (LE is luminous efficiency, EQE is external quantum efficiency, and PE is power efficiency). For lifetime testing, these devices were operated under a constant DC current corresponding to initial brightness level of 8,000 cd/m². The lifetime $LT_{80}$ is measured by the time elapsed for decay of brightness to 80% of the initial level.

TABLE 1

| Performance @ 1000 nits | Device 1 | Device 2 | Device 3 | Device 4 | Comp. Device 5 | Comp. Device 6 | Comp. Device 7 |
|---|---|---|---|---|---|---|---|
| Voltage | 7.9 | 7 | 8.4 | 7.3 | 6 | 6.4 | 7.4 |
| LE (cd/A) | 28 | 34 | 23 | 26 | 51 | 43 | 37 |
| EQE (%) | 7.5 | 9.2 | 6.3 | 6.9 | 13.9 | 11.7 | 11.7 |
| PE (lm/W) | 10.8 | 15.1 | 8.6 | 10.9 | 27 | 21.5 | 21.5 |
| $LT_{80}$ @ 8k nits | 72 | 99 | 48 | 59 | 79 | 78 | 1 |

In the above devices, the hole blocking material BL1 is more electron conducting than the hole blocking material BL2. One of the other notable results of this experiment is that the more electron conducting blocking layer of BL1 gives better performance with respect to efficiency, voltage, and lifetime (comparison of devices 1 and 2 with devices 3 and 4). Therefore, the use of a hole blocking layer may further improve device performance in the present invention.

As explained above, experimental devices 1-4 were made using HIL1 and HIL2 processed in ambient air. This ability to cure the film in air can be an advantage because it reduces the processing needs for making the device. If the conventional HIL3 were to be processed in air, the performance of the resulting device would be very poor. In comparative device 7, the PEDOT:PSS hole injection layer was processed in air and the device had a very short lifetime.

Materials used for making the devices:

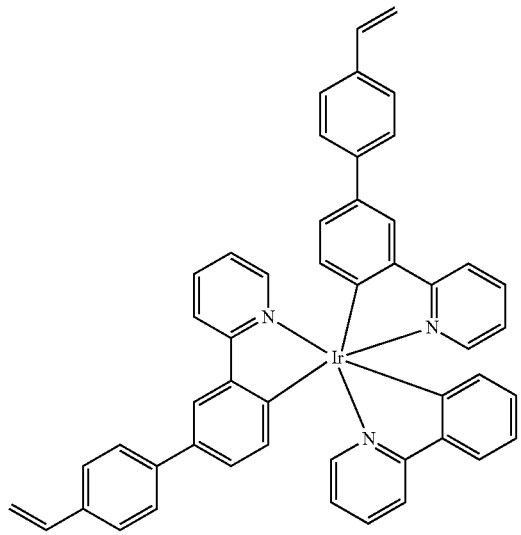

Conducting Dopant 1

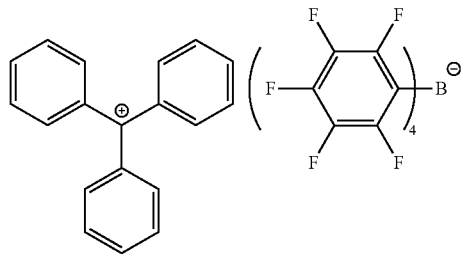

Compound B

HTL-1
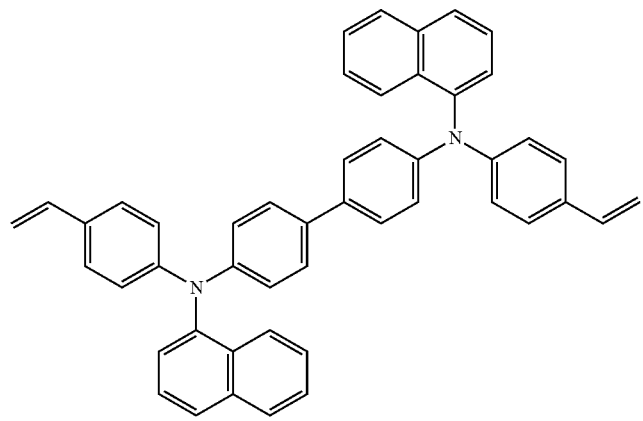
Host-1
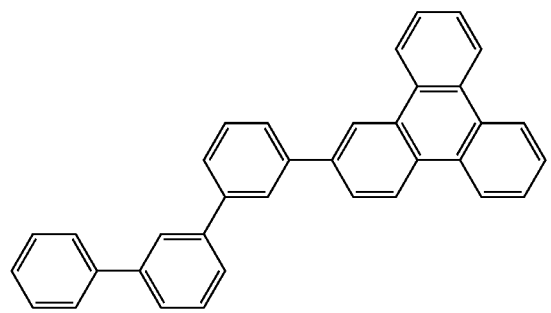
(A)
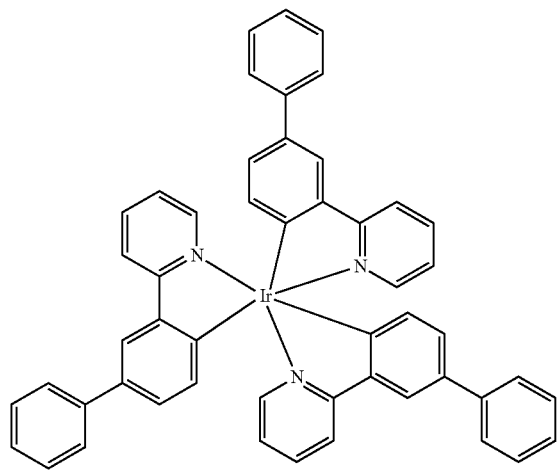

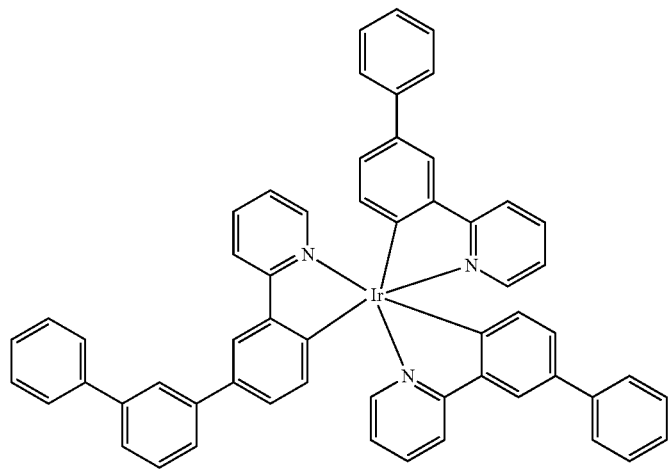
(B)
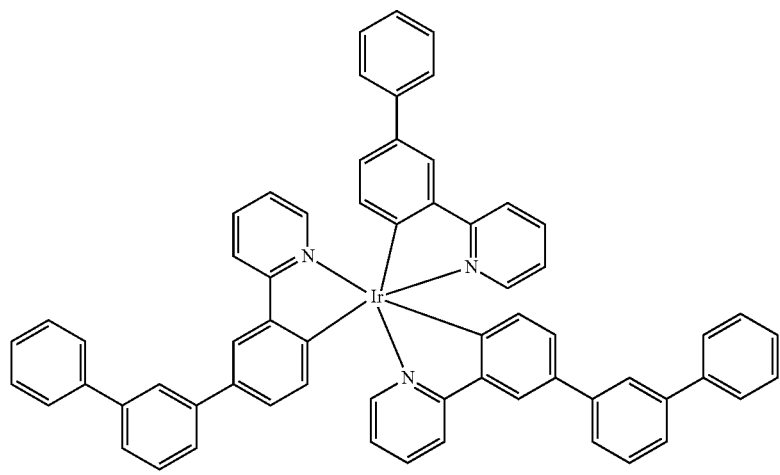
(C)
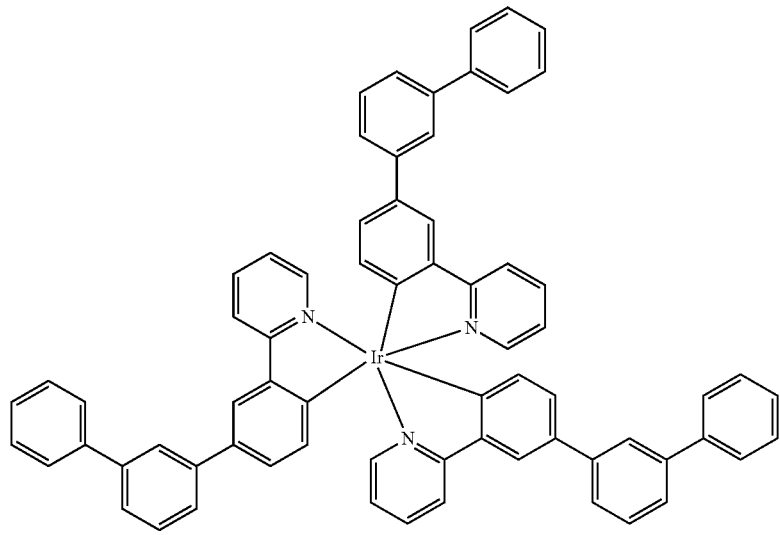
(D)

Green Dopant-1 is a mixture of A, B, C, and D in a ratio of 1.9:18.0:46.7:32.8

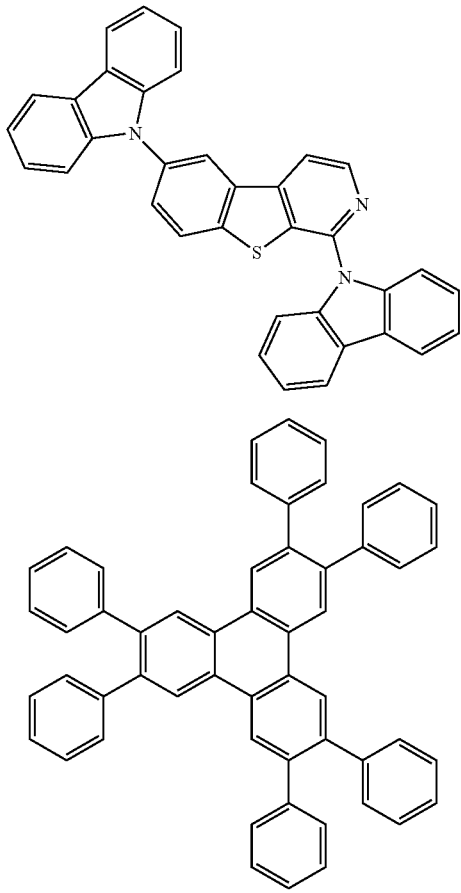

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

We claim:

1. An organic electronic device comprising:
a first electrode;
a second electrode; and
a covalently bonded composite organic/inorganic layer between the first and second electrodes, wherein the covalently bonded composite organic/inorganic layer comprising a metal-organic material comprising a metal alkoxide bonded to a triarylamine moiety having a hydroxyl group by stable coordination bonds, wherein in the metal-organic material, all stable coordination bonds with the metal atom of the metal alkoxide compound are covalent metal-oxygen-carbon bonds.

2. The device of claim 1, wherein the charge transport compound is a hole transport compound and the composite layer is a hole injection layer.

3. The device of claim 2, wherein the metal alkoxide is a vanadium alkoxide, a molybdenum alkoxide, or a titanium alkoxide.

4. The device of claim 1, wherein the charge transport compound is an electron transport compound and the composite layer is an electron injection layer.

5. The device of claim 1, wherein the composite layer is a hole injection layer directly adjacent the first electrode.

6. The device of claim 5, wherein the hole injection layer has a thickness of 50-750 Å.

7. The device of claim 1, wherein the device is an organic light-emitting device.

8. The device of claim 7, further comprising an emissive layer between the composite layer and the second electrode.

9. The device of claim 8, wherein the composite layer is a hole injection layer directly adjacent the first electrode.

10. The device of claim 8, wherein the emissive layer comprises a phosphorescent emitting dopant.

11. The device of claim 8, wherein the emissive layer comprises a fluorescent emitting compound.

12. The device of claim 8, further comprising a hole blocking layer between the emissive layer and the second electrode.

13. The device of claim 1, wherein the metal alkoxide is a vanadium alkoxide or a molybdenum alkoxide.

14. A covalently bonded composite organic/inorganic layer comprising a metal-organic material comprising a metal alkoxide bonded to a triarylamine moiety having a hydroxyl group by stable coordination bonds, wherein in the metal-organic material, all stable coordination bonds with the metal atom of the metal alkoxide compound are covalent metal-oxygen-carbon bonds.

15. The covalently bonded composite organic/inorganic layer of claim 14, wherein the metal alkoxide is a vanadium alkoxide or a molybdenum alkoxide.

16. The composite layer of claim 14, wherein the charge transport compound includes a triarylamine moiety.

* * * * *